US006805782B2

(12) United States Patent
Tanaka et al.

(10) Patent No.: US 6,805,782 B2
(45) Date of Patent: Oct. 19, 2004

(54) COMPOUND LAYERED TYPE OF SENSING DEVICE FOR MULTIPLE MEASUREMENT

(75) Inventors: Akio Tanaka, Gifui (JP); Toshitaka Saito, Toyohashi (JP); Akira Miyashita, Handa (JP); Keigo Mizutani, Okazaki (JP)

(73) Assignees: Denso Corporation, Kariya (JP); Nippon Soken, Inc., Nishio (JP)

( * ) Notice: Subject to any disclaimer, the term of this patent is extended or adjusted under 35 U.S.C. 154(b) by 0 days.

(21) Appl. No.: 09/820,819

(22) Filed: Mar. 30, 2001

(65) Prior Publication Data

US 2001/0025788 A1 Oct. 4, 2001

(30) Foreign Application Priority Data

Mar. 31, 2000 (JP) .......................................... 2000-098050
Mar. 13, 2001 (JP) .......................................... 2001-070834

(51) Int. Cl.[7] ............................................ G01N 27/407
(52) U.S. Cl. ......................... 204/424; 204/425; 204/427
(58) Field of Search ................................. 204/421–429

(56) References Cited

U.S. PATENT DOCUMENTS 4,755,274 A * 7/1988 Mase et al.
4,882,033 A * 11/1989 Shibata et al.
5,672,811 A    9/1997 Kato et al.
5,928,494 A * 7/1999 Kato et al.
6,319,377 B1 * 11/2001 Hasei et al.

FOREIGN PATENT DOCUMENTS

JP           2885336           2/1999

* cited by examiner

Primary Examiner—Kaj K. Olsen
(74) Attorney, Agent, or Firm—Nixon & Vanderhye, PC (57) ABSTRACT

In order to raise accuracy of measurement, a compound layered type of sensing device is provided. The device comprises a plurality of solid electrolyte plates and first to third electrochemical cells. Each cell has a single pair of electrodes disposed on the solid electrolyte plates. A concentration of a gas specified from a gas to be measured pre-processed based on oxygen pumping by the first electrochemical cell is detected by the second electrochemical cell. A difference in electromotive force between the gas to be measured and a reference gas is detected by the third electrochemical cell. The single pair of electrodes of the third electrochemical cell is disposed on the same surface of one of the solid electrolyte plates, and both of the first and third electrochemical cells are located with different ones of the solid electrolyte plates.

13 Claims, 10 Drawing Sheets

(SECOND ELECTROCHEMICAL CELL)

FIG. 5

(FIRST ELECTROCHEMICAL CELL)

FIG. 6

(THIRD ELECTROCHEMICAL CELL)

COMPOUND LAYERED TYPE OF SENSING DEVICE FOR MULTIPLE MEASUREMENT

BACKGROUND OF THE INVENTION

The present invention relates to a compound layered type of sensing device used for multiple measurement, and in particular, to such a sensing device which can be disposed in the exhaust gas system of an automobile internal combustion engine in order to detect the concentration of NOx contained in its exhaust gas, an air fuel ratio and other characteristics.

There has been known a gas sensor disposed in the exhaust system of an automobile internal combustion engine and configured to detect not only the concentration of NOx contained in its exhaust gas but also the concentration of oxygen contained in the exhaust gas in the form of a λ-characteristic. This gas sensor is very effective, because physical quantities, such as the concentration of NOx, an A/F (air fuel ratio), and a λ-characteristic can be detected by the same single sensor.

Figure 1:
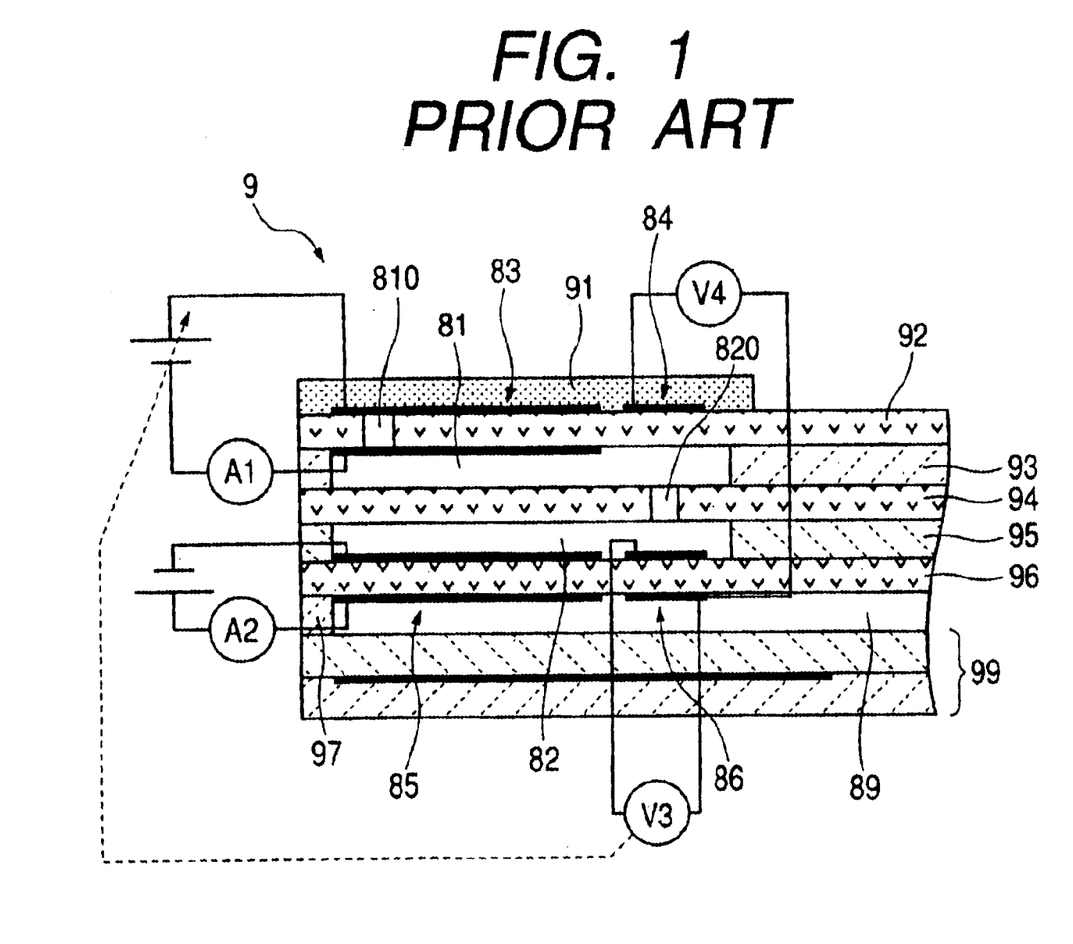
FIG. 1 shows the configuration of a conventional compound layered type of sensing element, part of which layered configuration is shown by a sectional view.

As a compound layered type of sensing device used for such a gas sensor, a four-sell type of device has been known conventionally, of which sectional configuration is shown in FIG. 1. As shown therein, this device 9 has a porous substrate 91, solid electrolyte plate 92, spacer 93, substrate 94, spacer 95, solid electrolyte plate 96, spacer 97, and layered type of heater 99, which are stacked in turn.

The sensing device 9 has a first chamber 81 and a second chamber 82, in addition to a reference gas chamber 89 in which a reference gas is charged. The first chamber 81 communicates with the outer space of the device 9 through a first diffusive resistance passage 810, while the second chamber 82 communicates with the first chamber 81 through a second diffusive resistance passage 820.

Additionally, the sensing device 9 has a first electrochemical cell 83, located therein so as to be exposed to the first chamber 81, that is capable of pumping oxygen from the outer space depending on an applied voltage thereto. The sensing device 9 also has a second electrochemical cell 85, located therein so as to be exposed to the second chamber 82, that is capable of outputting current corresponding to the concentration of NOx contained in an exhaust gas in response to a specified voltage applied thereto.

The sensing device 9 has also a third electrochemical cell 84 formed so that it is able to measure the concentration of an exhaust gas exhausted outside the device. Also, in the sending device 9 is provided a fourth electrochemical cell 86 that is exposed to the second chamber 82 and has the function of monitoring the concentration of oxygen present in the second chamber 82.

An electromotive force provided by the fourth electrochemical cell 86 is used to control voltage to be applied to the first electrochemical cell 83.

This type of sensing device makes it possible to measure the concentration of oxygen contained in an exhaust gas together with the concentration of NOx contained in an exhaust gas, so that a λ-characteristic and air fuel ratio can be obtained. Since the single sensor enables parallel measurement of both concentration of NOx and λ-characteristic (or air fuel ratio), providing the device with saved space and reducing a fitting cost of the device.

However, the foregoing compound layered type of sensing device has a drawback of being fairly low in accuracy of measurement of oxygen concentration, whereby being also low in accuracy of measurement of the λ-characteristic.

This drawback is mainly results because the first and third electrochemical cells 83 and 84 are located on the same solid electrolyte plate. The voltage applied to the first electrochemical cell 83 fluctuates and its output is fairly larger in amount than that of the third electrochemical cell 84, which largely influences the output of the third electrochemical cell 84.

As understood from FIG. 1, a total of five plates ranging from the first solid electrolyte plate 92 to the second one 96 are present between two electrodes of the second electrochemical cell 85. This presence gives rise to a larger amount of inner resistance to the second electrochemical cell, making the second electrochemical cell liable to influences of surrounding conditions such as temperature.

SUMMARY OF THE INVENTION

Therefore, an object of the present invention is to solve the foregoing drawback owned by the conventional sensing device, and to provide a compound layered type of sensing device capable of measuring the λ-characteristic with precision.

Another object of the present invention is to provide a compound layered type of sensing device capable of measuring the λ-characteristic with precision by detecting oxygen concentration more accurately.

Still another object of the present invention is to provide a compound layered type of sensing device, which is directed to multiple detection purposes, capable of concurrently detecting various physical parameters relating to a gas to be measured, with influences of surrounding conditions suppressed.

In order to realize the object, as one aspect of the present invention, there is provided a compound layered type of sensing device, comprising: a plurality of solid electrolyte plates; and first to third electrochemical cells each having a single pair of electrodes disposed on the solid electrolyte plates, in which a concentration of a gas specified from a gas to be measured pre-processed based on oxygen pumping by the first electrochemical cell is detected by the second electrochemical cell and a difference in electromotive force between the gas to be measured and a reference gas is detected by the third electrochemical cell; wherein the single pair of electrodes of the third electrochemical cell is disposed on a same surface of one of the solid electrolyte plates, and both of the first and third electrochemical cells are located with different ones of the solid electrolyte plates.

In this configuration, the single pair of electrodes of the third electrochemical cell is placed on the same surface of the same solid electrolyte plate with the electrodes close to each other. Thus the inner resistance of the third electrochemical cell becomes smaller, thereby resisting influence of sensor output measuring devices and/or outer circuits. Further, the smaller inner resistance reduces influence of outside atmospheric temperature.

Further, disposing the one pair of electrodes of the third electrochemical cell in that way makes it possible that voltage applied to this cell is fixed at a constant magnitude, without changes over time. Outputs of the third electrochemical cell are therefore reluctant to fluctuations over time.

Because each of the first and third electrochemical cells is disposed with different solid electrolyte plates, the third electrochemical cell shows resistance to influence of temporal changes in voltage applied to the first electrochemical cell.

Hence, accuracy of detecting differences in electromotive force between the gas to be measured and the reference gas by the third electrochemical cell can be raised. The difference in electromotive force is proportional to the concentration of oxygen contained in the gas to be measured. When the compound layered type of seasoning device according to the present invention is disposed in the combustion exhaust system of an internal combustion engine, a λ-characteristic of the engine can be measure with precision the third electrochemical cell.

Additionally, the applied voltage to the first electrochemical cell may be controlled in such a manner that a map is produced in advance based on amounts of current obtained from the concentration of oxygen contained in a gas to be measured, and the applied voltage is controlled using the map. Higher accuracy is therefore secured in controlling the concentration of oxygen present in the chambers into a predetermined constant.

Thus a compound layered type of sensing device with higher accuracy of measurement of the λ-characteristic can be provided.

In the foregoing one aspect of the present invention, it is preferred that the device further comprises first and second chambers formed in the device and into which the gas to be measured is introduced, and a fourth electrochemical cell configured to detect the concentration of the oxygen present in at least one of the first and second chambers.

Hence, the fourth electrochemical cell is used for detecting the concentration of oxygen present in the first or second chamber and controlling the applied voltage to the first electrochemical cell. A gas to be measured can be measured in concentration with higher precision. Alternatively, correcting measurements acquired by the fourth electrochemical cell enables an objective gas to be measured in concentration with precision.

In this configuration, when the first and fourth electrochemical cells are made from inert electrodes (for example, made of Pt or Au) to a gas to be measured (NOx) and predetermined voltage is applied to both cells, the concentration of only oxygen present in the chambers can be measured. This measurement may be replaced by a technique of using electromotive force obtained from oxygen and a reference gas in the chambers.

Still, it is preferred that the first chamber communicates with an outside of the device via a first diffusive resistance passage and the second chamber communicates with the first chamber via a second diffusive resistance passage, the first electrochemical cell being configured, with one surface thereof exposed to the first chamber, so as to take oxygen in and out to and from the first chamber correspondingly to voltage applied to the first electrochemical cell, and the second electrochemical cell being configured, with one surface thereof exposed to the second chamber, so as to detect current corresponding to the concentration of the specified gas contained in the gas to be measured by applying a predetermined voltage to the second electrochemical cell.

According this configuration, the first electrochemical cell is able to control the concentration of oxygen existing in both of the first and second chambers to a constant amount. Fluctuations in oxygen concentration at both chambers cause disturbances to a gas to be measured. Hence, the control to a constant concentration enables measurement accuracy to be improved.

Accordingly, amounts of current corresponding to the concentration of a specified gas detected by the second electrochemical cell can be avoided from being influenced by the concentration of oxygen contained in a gas to be measured, even if the oxygen concentration fluctuates.

The first and second diffusive resistance passage can be formed with a porous member combined with a tiny through hole such as a pin hole.

Preferably, the device further comprises a plurality of reference chambers, wherein both of the second and fourth electrochemical cells are disposed to a same one of the reference gas chambers and either one of the first and second chambers.

This configuration permits the concentration of oxygen remaining within the first and second chambers to be measured accurately.

Still preferably, the device comprises a plurality of reference chambers, wherein each of the first and third electrochemical cells is disposed to a different one of the reference gas chambers.

Thus, without being affected by electric noise from the first electrochemical cell, the third electrochemical cell is able to perfume higher accurate measurement.

It is also preferred that an alumina-made plate intervenes between the first and second electrochemical cells so that both the cells are insulated to each other.

The first electrochemical cell is therefore insulated from the second electrochemical cell, whereby avoiding the second electrochemical cell from being influenced by voltage fluctuations or the like of the first electrochemical cell.

As another aspect of the present invention, there is provided a compound layered type of sensing device, comprising: first and second chambers into which a gas to be measured is introduced, the first chamber communicating with an outside of the device via a first diffusive resistance passage and the second chamber communicating with the first chamber via a second diffusive resistance passage; first and second reference gas chambers into which a reference gas is introduced; a first electrochemical cell, disposed to be exposed to the first chamber, for pumping oxygen correspondingly to voltage applied to the first electrochemical chamber; a second electrochemical cell, disposed to be exposed to the second chamber, for detecting current corresponding to a concentration of a gas specified in the gas to be measured by applying a predetermined voltage to the second electrochemical chamber; a third electrochemical cell for measuring a concentration of oxygen contained in the gas to be detected; and first and second solid electrolyte plates between which the first and second chambers are formed, wherein the first reference gas chamber is disposed on a surface of the first solid electrolyte plate facing the outside of the device and the second reference gas chamber is disposed to be exposed to the first and second chambers by way of the second solid electrolyte plate; the first electrochemical cell, disposed with the second solid electrolyte plate, has a pumping electrode exposed to the first chamber and a reference pumping electrode exposed to the second reference gas chamber; the second electrochemical cell, disposed with the first solid electrolyte plate, has a sensing electrode exposed to the second chamber and a reference sensing electrode exposed to the first reference gas chamber; and the third electrochemical cell, disposed with the first solid electrolyte plate, has an oxygen sensing electrode facing the outside of the device and a reference oxygen sensing electrode exposed to the first reference gas chamber, both of the oxygen sensing electrode and the reference oxygen sensing electrode being disposed on a same surface of the first solid electrolyte plate.

According to this aspect of the invention, the oxygen sensing and reference oxygen sensing electrodes of the third electrochemical cell are close to each other in distance. The inner resistance of the cell is therefore small. The third electrochemical cell shows resistance to influence of outer circuits and sensor output measuring apparatuses, thereby making a contribution to measurement with higher accuracy.

As stated before, a smaller-value of inner resistance of the third electrochemical cell reduces influence of outer atmospheric temperature, whereby leading to measurement of oxygen concentration with higher precision.

Further, it is the second electrochemical cell that is disposed with the first solid electrolyte plate with which the third electrochemical cell is disposed as well. Because the voltage applied to the second electrochemical cell is constant over time, the measurement accuracy of the third electrochemical cell has not so much influence from the second electrochemical cell.

Still further, the first electrochemical cell is located with the second solid electrolyte plate located with both first chamber and first solid electrolyte plate layered thereon. The third electrochemical cell has little influence of the fluctuating voltage applied to the first electrochemical cell.

This enables higher accuracy of measurement of the third electrochemical cell, whereby increasing the measurement accuracy of the λ-characteristic.

Therefore, it is possible for the present invention to provide a compound layered type of sensing device superior in the measurement accuracy of the λ-characteristic.

PREFERRED EMBODIMENTS OF THE INVENTION

Referring to the accompanying drawings, preferred embodiments of the present invention will now be described.

[1] First Embodiment

Referring to FIGS. 2 to 6, a compound layered type of sensing element of a first embodiment of the present invention will now be described.

Figure 2:
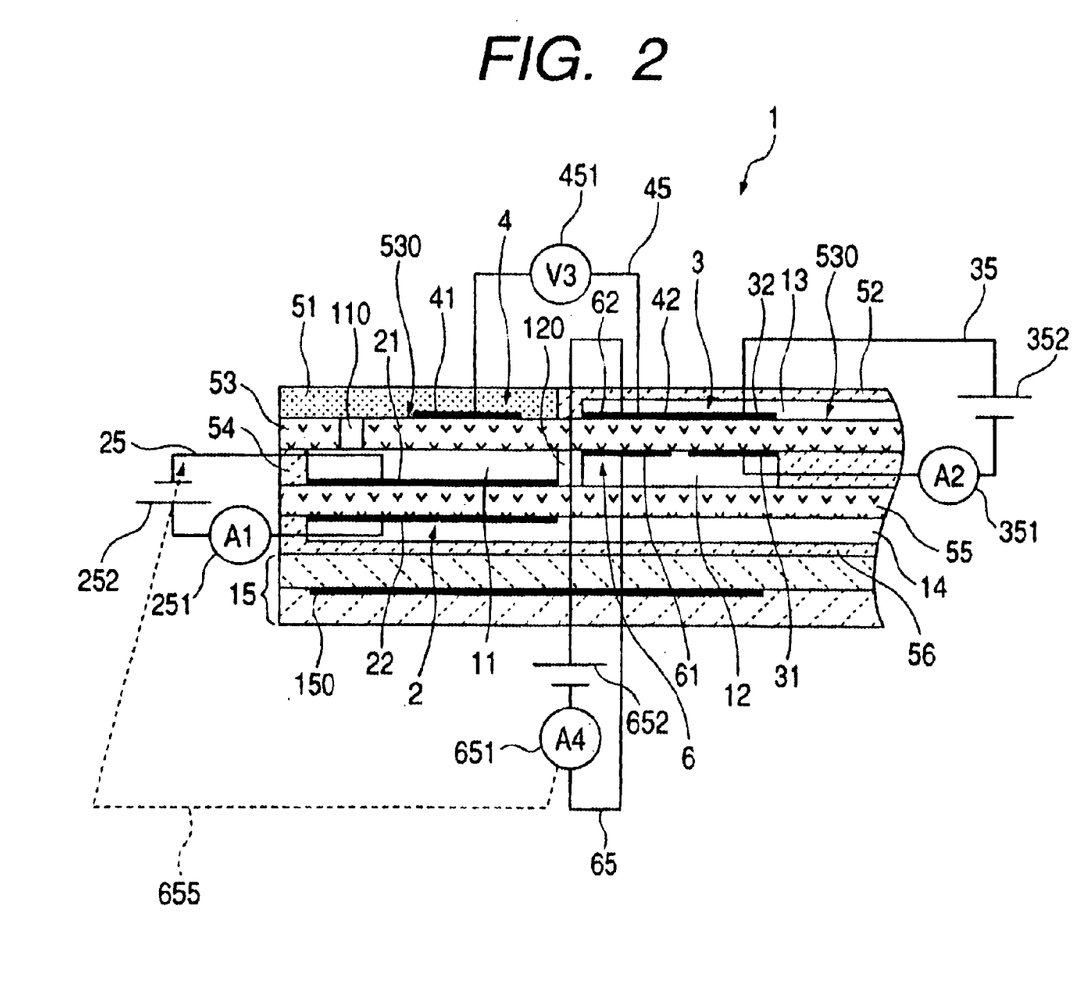
FIG. 2 shows the configuration of a compound layered type of sensing element according to a first embodiment of the present invention, part of which layered configuration is shown by a sectional view.

A compound layered type of sensing element 1 according to the present embodiment is shown in FIG. 2. This sensing element 1 has solid electrolyte plates 53 and 55 and a first to third electrochemical cells 2 to 4 each comprising a pair of electrodes 21 and 22, 31 and 32, or 41 and 42 secured on the plate 53 or 55. A gas to be measured is produced by pre-processing based on oxygen pumping carried out by the first electrochemical cell 2. The concentration of a specified gas is measured by the second electrochemical cell 3 from the gas to be measured. Concurrently, a difference between electromotive force of the gas to be measured and a reference gas is detected by the third electrochemical cell 4.

A pair of electrodes 41 and 42 of the third electrochemical cell 4 are disposed on the same surface 530 of the same solid electrolyte plate 53. The electrodes of each of the first and second electrochemical cells 2 and 3 are disposed on different surfaces of the solid electrolyte plate 53 or 55.

The configuration will now be detailed as follows.

The compound layered type of sensing element according to the present embodiment is used, by way of example, as a gas sensing element secured in the exhaust system of an automobile engine. The gas sensing element is used in parallel for measurement of the concentration of NOx treated as air pollutant and detection of the λ-characteristic and air fuel ratio of the engine.

The sensing device 1 comprises, as shown in FIG. 1, a porous plate 51, spacer 52, first solid electrolyte plate 53, spacer 54, second solid electrolyte plate 55, spacer 56, and heater 15.

Each of the spacers 52, 54 and 56 is composed of an alumina ceramic plate and each of the first and second solid electrolyte plates 53 and 55 is made of an oxygen-ion conductive zirconia ceramic martial. The heater 15 is a ceramic heater having alumina ceramic plates in which a heating device 150 is incorporated therein.

A through hole that serves as a first diffusive resistance passage 110 is formed through the first solid electrolyte plate 53. The porous plate 51 is located to cover the diffusive passage 110. The spacer 52 is disposed to be contiguous to the porous plate 51. Both spacer 52 and first solid electrolyte plate 53 form a first reference gas chamber 13 therebetween.

Figure 3:
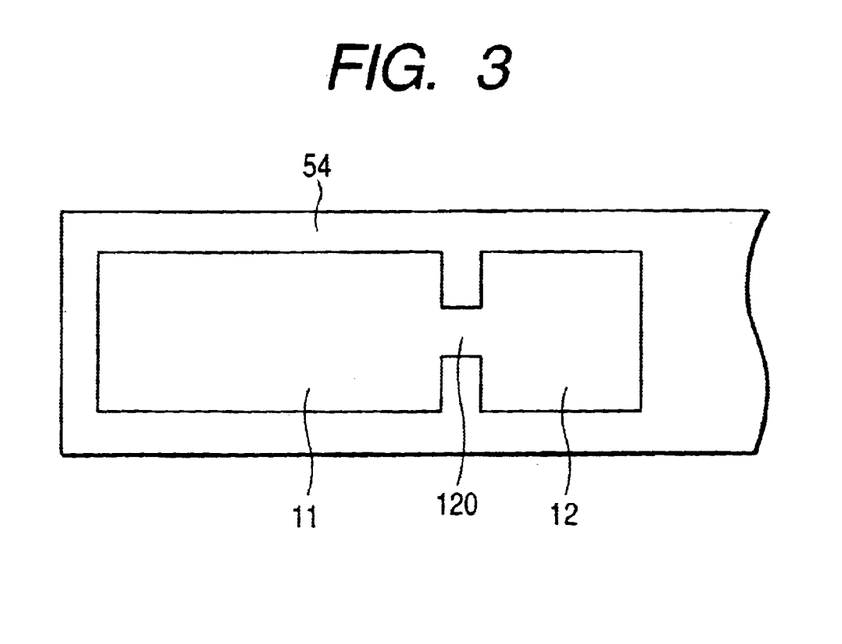
FIG. 3 is the plan view of a spacer used in the first embodiment.

Each of a first and second chambers 11 and 12 is formed as space partitioned by the first and second solid electrolyte plates 53 and 55 and the spacer 54. A second reference gas chamber 14 is made up of space partitioned by the second solid electrolyte plate 55 and the spacer 56. As shown in FIGS. 2 and 3, the first and second chambers 11 and 12 are connected through a second thin diffusive resistance passage 120.

The third electrochemical cell 4 functions as an oxygen density electromotive force type of battery.

In the third electrochemical cell 4, one electrode 41, located as an oxygen sensing electrode for a gas to be measured, is disposed between the first solid electrolyte plate 53 and the porous plate 51. The other electrode 42, which functions as a reference oxygen sensing electrode, is disposed so as to be exposed to the first reference gas chamber 13. The third electrochemical cell 4 is coupled with an oxygen sensing circuit 45 in which a voltmeter 451 is inserted.

The voltmeter 451 measures electromotive force caused between the first and second electrodes 41 and 42. This electromotive force is generated by differences in oxygen concentration between the atmosphere of a gas to be measured outside this sending device and the atmosphere in the first reference gas chamber. This electromotive force provides an output of the third electrochemical cell 4.

Figure 8:
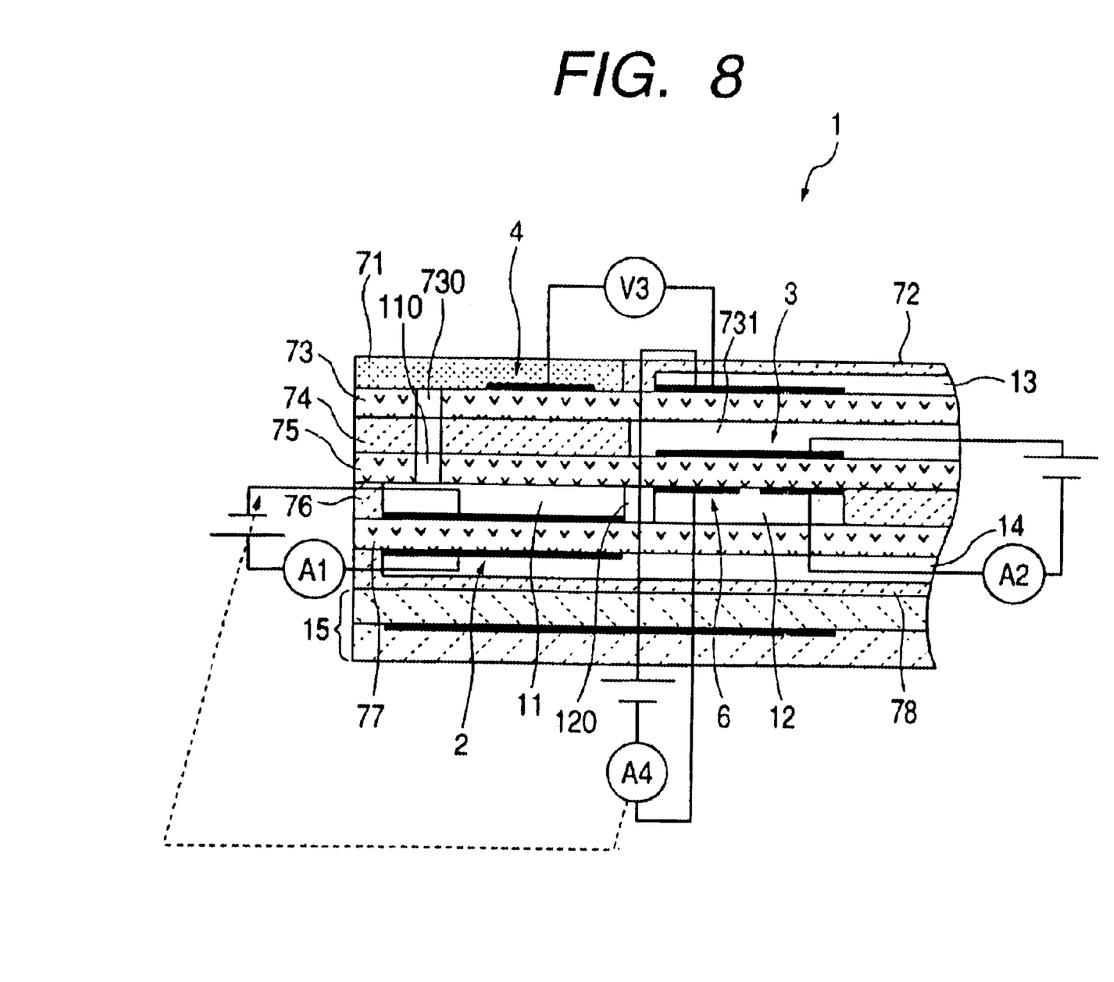
FIG. 8 shows the configuration of a compound layered type of sensing element according to a third embodiment configured using three solid electrolyte plates, part of which layered configuration is shown by a sectional view.

The first electrochemical cell 2 has a function as a pumping cell. This cell 2 receives a voltage signal supplied by an electric power source 252 feedback-controlled by current detected by an ammeter 651 of a fourth electrochemical cell 6, which will be described later. As a result, the cell 2 functions so that it takes in and takes out, between the first chamber 11 and the second reference gas chamber, oxygen in response to a value of the applied voltage signal. As anther example of this pumping, feedback control using pumping current and a previously set map as shown in FIG. 8.

The first electrochemical cell 2, disposed with the second solid electrolyte plate 55, comprises the measured-gas-side pumping electrode 21 exposed to the first chamber 11 and the reference pumping electrode 22 exposed to the second reference gas chamber 14. Between the electrodes 21 and 22, a pumping circuit 25 in which an ammeter 251 and an electric power source 252 are inserted in series is provided. A feedback circuit 655 is provided between a later-described ammeter 651 and the electric power source 252.

Pumping electric current corresponds to the concentration of oxygen present in the first chamber 11. The electric power source 252 is controlled so that current in the fourth electrochemical cell 6 is kept at a constant amount through the feedback circuit 655. This control permits the first electrochemical cell 2 to keep the concentration of oxygen in the first chamber 11, that is, in the second chamber 12 communicating with the first one 11, at a constant amount.

The measured-gas-side pumping electrode 21 is an inert electrode against NOx, so that no diffusion gives to NOx.

The second electrochemical cell 3 receives constant voltage of which amount unchanged over time, and measures the concentration of NOx using oxygen-ion current that generates due to the constant current.

This cell 3, disposed with the first solid electrolyte plate 53, comprises the measured-gas-side sensing electrode 31 exposed to the second chamber 12 and the reference sensing electrode 32 exposed to the first reference gas chamber 13. Between the electrodes 31 and 32, a sensing circuit 35 in which an ammeter 351 and an electric power source 352 are inserted in series is provided.

Moreover, the reference sensing electrode 32 is formed as an integrated electrode with the reference oxygen sensing electrodes 42 and 62 which will be described later.

The measured-gas-side sensing electrode 31 is an active electrode which is able to decompose NOx into nitrogen and oxygen. Applying voltage to the second electrochemical cell 3 causes oxygen ions to be yielded on the surface of the measured-gas-side sensing electrode 31, and the oxygen ions communicates as ion current through the first solid electrolyte plate 53. Hence, the ammeter 351 can measure the ion current.

The ion current is proportional to the concentration of NOx contained in the gas to be measured, unless the measured-gas-side pumping electrode 21 of the first electrochemical cell 2 decomposes NOx. As a result, readings of the ammeter 351 provide NOx concentration.

By the way, oxygen contained in the gas to be measured is decomposed on the measured-gas-side sensing electrode 31. However, ion current inherent to NOx can be measured correctly if calibration is made in advance, because the concentration of oxygen in the gas to be measured is substantially kept constant by the first electrochemical cell 2. The calibration is done by measuring a reading of the ammeter 351 in the condition that the concentration of NOx is kept zero.

Alternatively, the foregoing correct measurement of ion current can also be realized by correction which uses an amount of current through the fourth electrochemical cell 6. That is, the correction is made such that an amount of current through the fourth electrochemical cell 6, which corresponds to a residual oxygen concentration in the chamber 12, is deducted from a measurement of the ion current.

The fourth electrochemical cell 6, which functions as a cell for pumping oxygen, is configured so as to measure the concentration of oxygen present in the second chamber 12.

To be specific, the fourth electrochemical cell 6, which is disposed with the first solid electrolyte plate 53, has the measured-gas-side sensing electrode 61 exposes to the second chamber 12 and the reference sensing electrode 62 exposed to the first reference gas chamber 13. A sensing circuit 65 into which the ammeter 651 and an electric power source 652 is inserted in series is provided between the electrodes 61 and 62. In addition, the feedback circuit 655 is provided to connect the ammeter 651 to the foregoing power source 252. The measured-gas-side sensing electrode 61 is formed into an inert electrode to NOx.

The fourth electrochemical cell 6 detects current by using the ammeter 651, the current being caused correspondingly to a value of oxygen concentration in the second chamber 12. The detected current is used by the feedback circuit 655 to control a pumping operation performed by the first electrochemical cell 2.

The principle of operation of this compound layered type of sensing device 1 will now be described.

An exhaust gas, which is an objective gas to be measured, is introduced into the first chamber 11 through the porous plate 51 and first diffusive resistance passage 110, and diffused therein. The introduced exhaust gas is also diffused into the second chamber 12 via the second diffusive resistance passage 120. This exhaust gas includes NOx, oxygen, HC, and others.

The first electrochemical cell 2 is exposed to the first chamber 11, whilst the fourth electrochemical cell 6 to the second chamber 12. Hence, the fourth electrochemical cell 6 produces current responsively to the concentration of oxygen present in the second chamber 12. The produced current is detected by the ammeter 651, providing a reading A4 of the current.

Based on the reading A4, which fluctuates depending on fluctuations in the concentration of oxygen, the feedback circuit 655 controls the power source 252 of the first electrochemical cell 2.

The power source controls operations of taking in and out oxygen between the first chamber 11 of the first electrochemical cell 2 and the second reference gas chamber 14. Thus, the concentration of oxygen becomes the same between the first chamber 11 and the second chamber 12. The control is done such that if the oxygen concentration is lean, oxygen ions are moved to the second reference gas chamber 14, while if the oxygen concentration is rich, oxygen ions are mode to the first chamber 11.

Figure 5:
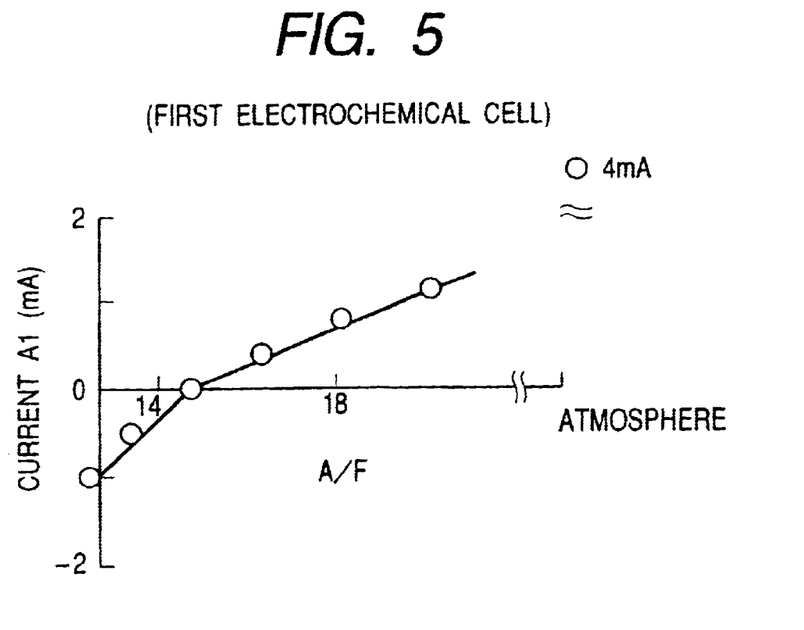
FIG. 5 is a graph representing a relationship between an air and fuel ratio and current generated by a first electrochemical cell in the first embodiment.

Responsively to the above taking-in and taking-out of oxygen, oxygen ion current flows through the first electrochemical cell 2, and the current is detected by the ammeter 251. FIG. 5 shows the relationship between the readings of current of an air fuel ratio at an exhaust gas system. Therefore, the outputs of the first electrochemical cell 2 are used to measure the air fuel ratio.

In contrast, in the second electrochemical cell 3 exposed to the second chamber 12, NOx present in the exhaust gas is decomposed by the electrode 31. The decomposition causes oxygen ions to be generated, so its ion current is measured by the ammeter 351.

Figure 4:
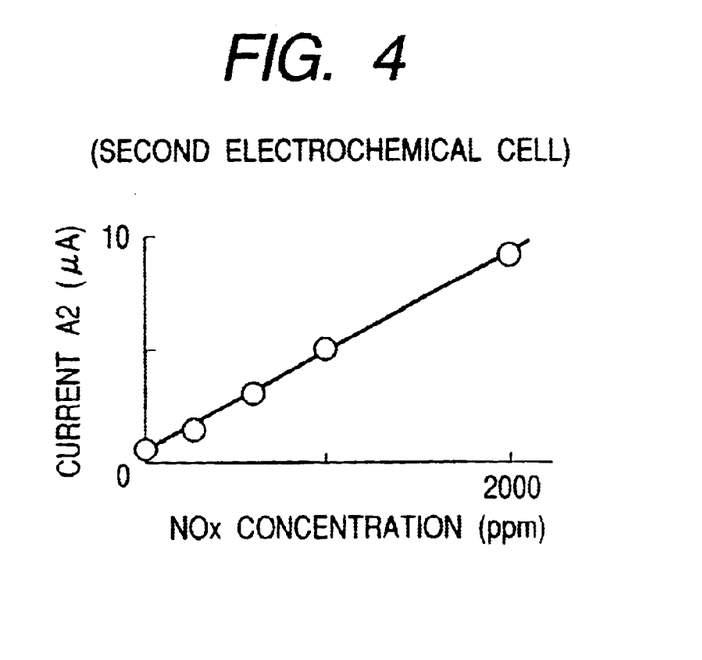
FIG. 4 is a graph representing a relationship between the concentration of NOx and current generated by a second electrochemical cell in the first embodiment.

An amount A2 of this ion current is in proportion to the concentration of NOx in the exhaust gas. The correspondence between the ion current and the concentration of NOx is shown in FIG. 4.

Figure 6:
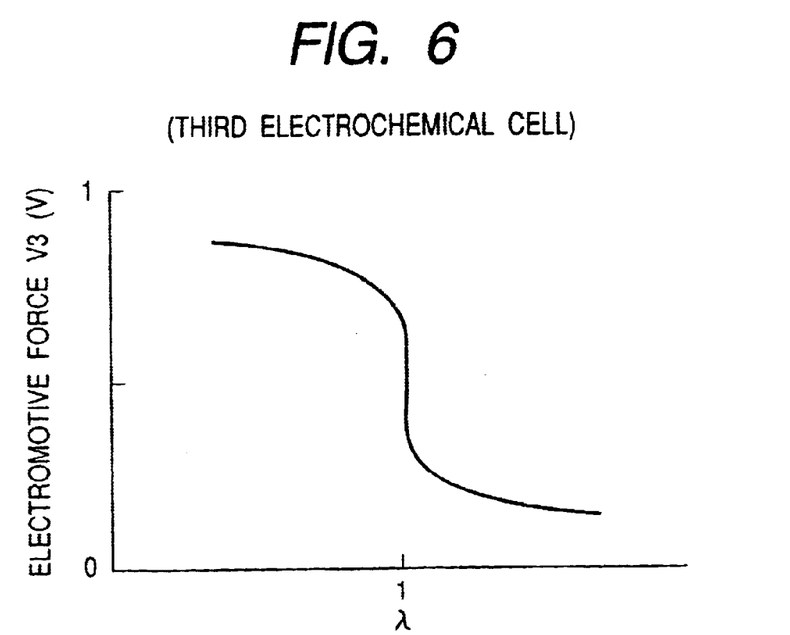
FIG. 6 is a graph representing a relationship between a λ-characteristic and an electromotive force generated by a third electrochemical cell in the first embodiment.

Concurrently, in the third electrochemical cell 4, electromotive force is generated correspondingly to differences between the concentration of oxygen in the first reference gas chamber 13 and that of the exhaust gas before introduced into the first chamber 11. This electromotive force is measured by the voltmeter 451. A reading V3 of this voltage corresponds to λ in the exhaust gas system. The relationship between the electromotive force and the λ is shown in FIG. 6.

The advantages of the embodiment are as follows.

The single pair of electrodes 41 and 42 of the third electrochemical cell 4 is disposed on the same surface 530 of the first solid electrolyte plate 53 and closely to each other. As a result, the inner resistance of the third electrochemical cell 4 is low in magnitude, has resistance to influence from outside the element, and provides outputs in a stable fashion. Moreover, since the third electrochemical cell 4 is free from temporal fluctuations in the voltage applied thereto, its outputs are also almost free from fluctuations over time, providing stable outputs.

Further, the first and third electrodes 2 and 4 are disposed on the different solid electrolyte plates, so that the third electrochemical cell 4 resists influence of the applied voltage to the first electrochemical cell 2.

Therefore, according to the present embodiment, when detecting electromotive force generated between a gas to be measured and a reference gas by the third electrochemical cell 4, its detection accuracy can be raised, and the λ-characteristic is therefore can be detected with precision.

The present invention is therefore able to provide the compound layered type of sensing device which is superior in the accuracy of measurement of the λ-characteristic.

In addition, the fourth electrochemical cell 6 is provided in the sensing device, which enables an oxygen concentration in the second chamber 12 to be measured. It is therefore possible to control the first electrochemical cell 2 with precision based on such measurements and to detect an air fuel ratio of a gas to be measured. This eliminates the necessity for disposing a separate air-fuel-ratio sensor, providing a superior sensing device on a cost.

[Second Embodiment]

Figure 7:
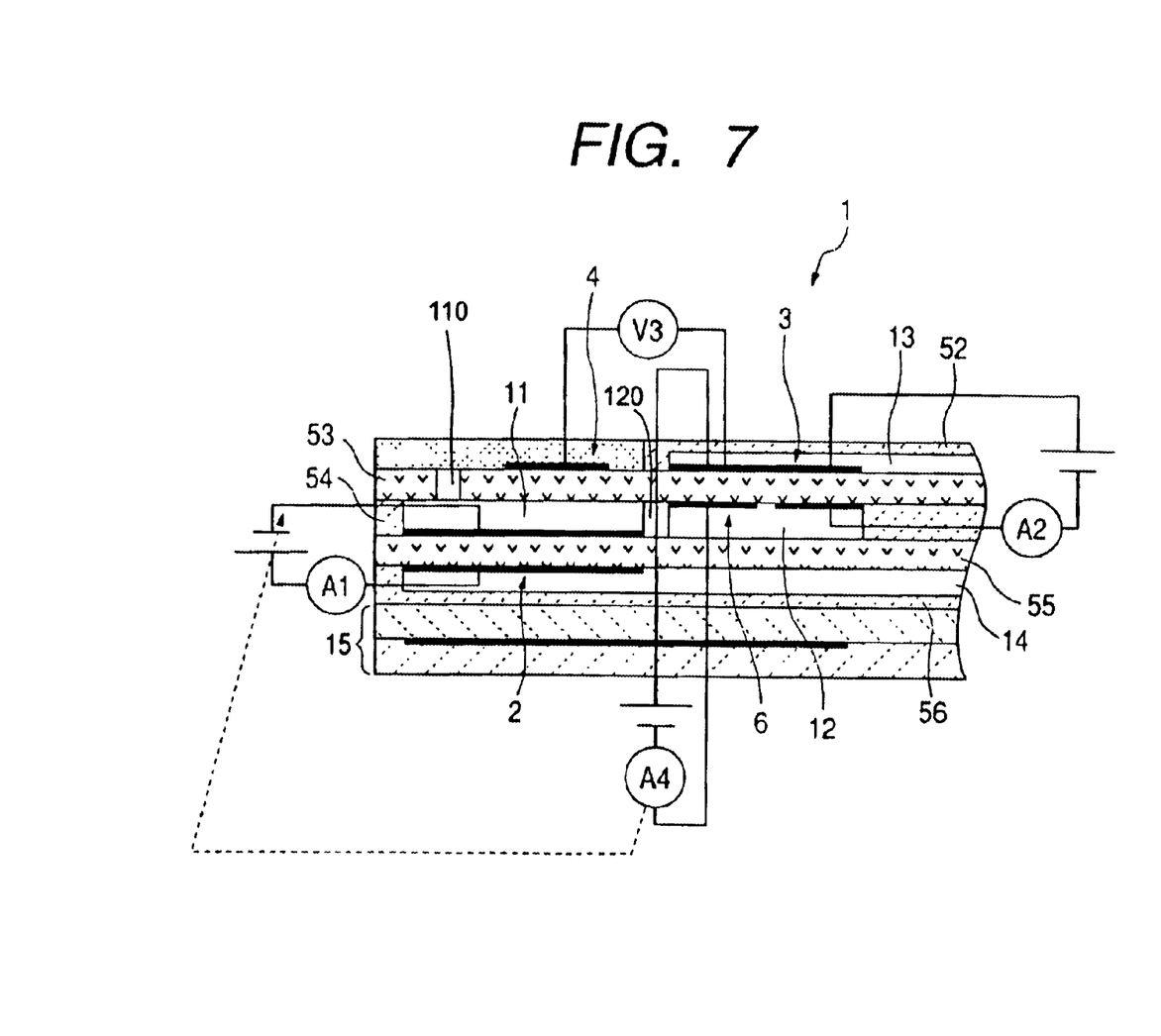
FIG. 7 shows the configuration of a compound layered type of sensing element according to a second embodiment configured using zirconia ceramics, part of which layered configuration is shown by a sectional view.

Referring to FIG. 7, a second embodiment of the present invention will now be described.

As shown in FIG. 7, the second embodiment a layered type of sensing device of which configuration is identical to that of the first embodiment, except in that materials composing the spacers and plates are different.

Specifically, in the compound layered type of sensing device 1 of the present embodiment, the spacers 52, 54 and 56 and the first and second solid electrolyte plates 53 and 55 are made of a zirconia ceramic material. In addition, the heater 15 is also made of a zirconia ceramic material.

The others are identical to those in the first embodiment, so, compared to the first embodiment, the sensing device of the second embodiment operates in a similar way and has the identical advantages.

As stated, because all the layered constituents are made of a zirconia ceramic material, the sensing device 1 has resistance to cracks in the device which are caused due to thermal stress occurring between or among layers of which materials differ from each other.

[Third Embodiment]

Referring to FIG. 8, a third embodiment of the present invention will now be described.

A compound layered type of sensing device 1 of the present embodiment is shown in FIG. 8, in which the first to third electrochemical cells are disposed with mutually different solid electrolyte plates.

This sensing device 1 has a porous plate 71, spacers 72, 74, 76 and 78, three solid electrolyte plates 73, 75 and 77, and heater 15.

A measured-gas-side space 731 is formed by the solid the electrolyte plates 73 and 75, and the spacer 74, and a gas to be measured is introduced into the space 731 from the outside via a passage 730 formed through the solid electrolyte plate 73.

The first chamber 11 and the second chamber 12 is formed by the solid electrolyte plates 75 and 77, and spacer 76. The gas to be measured enters the first chamber 11 from the measured-gas-side space 731 through the first diffusive resistance passage 110.

The first electrochemical cell 2, which is disposed with the solid electrolyte plate 77, is located so to be exposed to the first chamber 11 and the second reference gas chamber 14. The second electrochemical cell 3, which is disposed with the solid electrolyte plate 75, is located so to be exposed to the second chamber 11 and the measured-gas chamber 731.

The third electrochemical cell 4, which is disposed with the solid electrolyte plate 73, is located to face the porous plate 71 and to be exposed to the first reference gas chamber 13. The fourth electrochemical cell 6, which is disposed with the solid electrolyte plate 75, is located to be exposed to the second chamber 12 and the measured-gas-side space 731. The remaining constituents are identical to those of the first embodiment.

As stated above, in this sensing device 1, the first to third electrochemical cells 2, 3 and 4 are disposed with the different solid electrolyte plates 73, 75 and 77. Hence it is prevented that current passing through each cell interferes with the other cells.

Therefore, the concentration of NOx, λ-characteristic, air-fuel ratio, and others can be measured with a higher precision, in addition to the similar operations and advantages to those of the first embodiment.

[Fourth Embodiment]

Referring to FIGS. 9 to 13, a fourth embodiment of the present invention will now be described.

Figure 9:
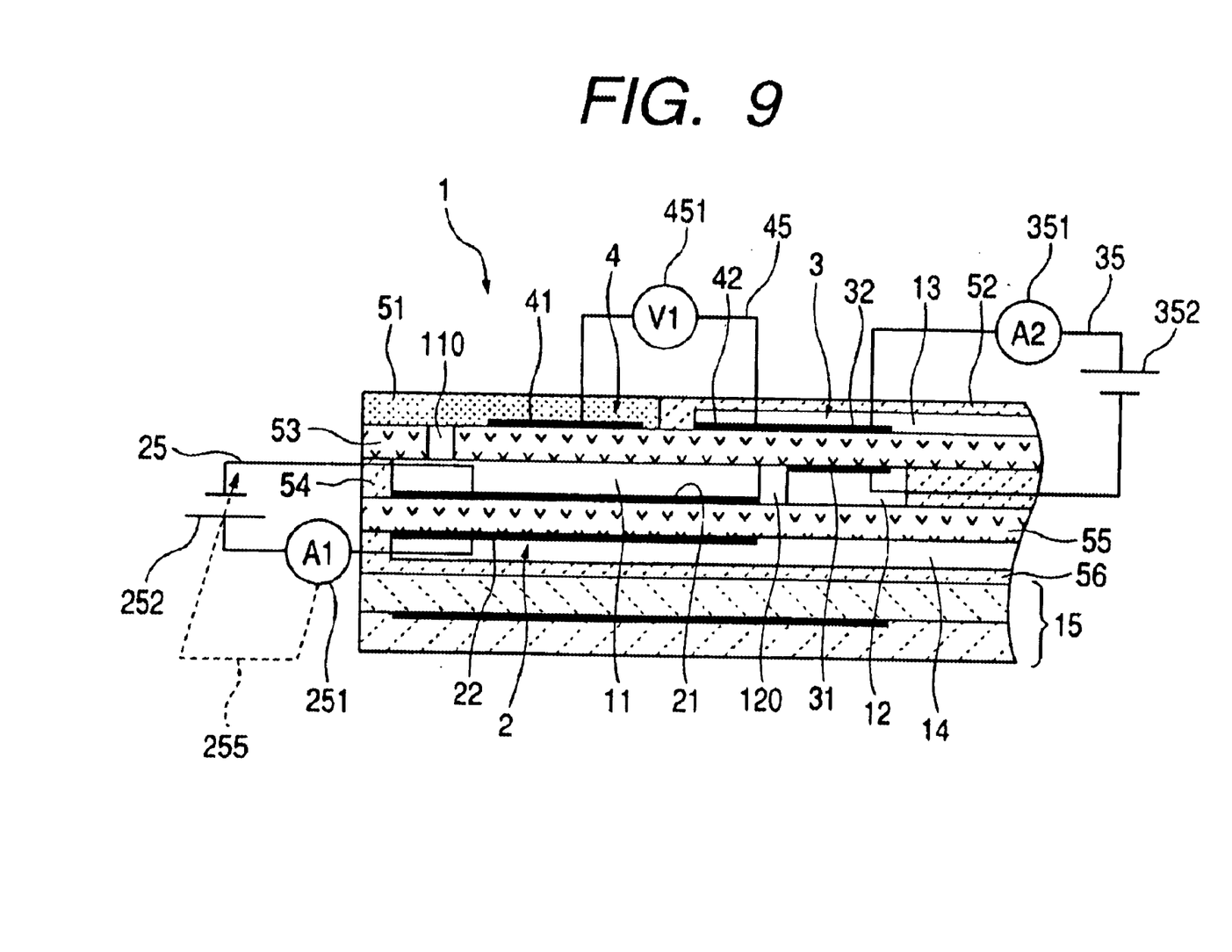
FIG. 9 shows the configuration of a compound layered type of sensing element according to a fourth embodiment, part of which layered configuration is shown by a sectional view.

FIG. 9 shows a compound layered type of sensing device 1 according to the present embodiment. As shown in 9, this sensing devise 1 has the first and second chambers 11 and 12 into which a gas to be measured is introduced and the first and second reference gas chambers 13 and 14 into which a reference gas is introduced.

The first chamber 11 is formed to communicate with the outside of the device by way of the first diffusive resistance passage 110. On the other hand, the second chamber 12 is formed to communicate with the first chamber 11 through the first diffusive resistance passage 120.

The sensing device 1 has the first electrochemical cell 2 formed to be exposed to the first chamber 11 and capable of pumping oxygen correspondingly to a magnitude of applied voltage. The sensing device has also the second electrochemical cell 3 formed to be exposed to the second chamber 12 and capable of supplying current corresponding to the concentration of a specified gas within the gas to be measured. Further, the sensing device has the third electrochemical cell 4 formed to measure the concentration of oxygen present within the gas to be measured.

The first and second chambers 11 and 12 are formed to be sandwiched between the first and second solid electrolyte plates 53 and 55. The first reference gas chamber 13 is formed with the outside surface of the first solid electrolyte plate 53 as its one partition. The second reference gas chamber 14 is formed using as its one perdition the opposite side surface of the second solid electrolyte plate 55 to the first and second chambers 11 and 12.

The first electrochemical cell 2, disposed with the second solid electrolyte plate 55, comprises the measured-gas-side pumping electrode 21 exposed to the first chamber 11 and the reference pumping electrode 22 exposed to the second reference gas chamber 14.

The second electrochemical cell 3, disposed with the first solid electrolyte plate 53, comprises the measured-gas-side sensing electrode 31 exposed to the second chamber 12 and the reference sensing electrode 32 exposed to the first reference gas chamber 13.

The third electrochemical cell 4 has the measured-gas-side oxygen sensing electrode 41 disposed on the first solid electrolyte plate 53 so as to face the outside of the device and the reference oxygen sensing electrode 42 located to be exposed to the first reference gas chamber 13.

Both of the measured-gas-side oxygen sensing electrode 41 and reference oxygen sensing electrode 42 are disposed on the same surface of the same first solid electrolyte plate 53.

The configuration will now be detailed as follows.

The compound layered type of sensing element 1 according to the present embodiment is used, by way of example, in a gas sensor secured in the exhaust system of an automobile engine. The gas sensor is used for measurement of the concentration of NOx, in addition to measurement of the concentration of in an exhaust gas, air fuel ratio, λ-characteristic.

The sensing device 1 comprises, as shown in FIG. 9, the porous plate 51, spacer 52, first solid electrolyte plate 53, spacer 54, second solid electrolyte plate 55, spacer 56, and heater 15.

Each of the spacers 52, 54 and 56 is composed of an alumina ceramic plate and each of the first and second solid electrolyte plates 53 and 55 is made of an oxygen-ion conductive zirconia ceramic material. The heater 15 is a ceramic heater having insulating alumina ceramic plates in which a heating device is incorporated therein.

The through hole that serves as the first diffusive resistance passage 110 is formed through the first solid electrolyte plate 53. The porous plate 51 is located to cover the diffusive passage 110. The spacer 52 is disposed to be contiguous to the porous plate 51. Both spacer 52 and first solid electrolyte plate 53 form the first reference gas chamber 13 therebetween.

Each of the first chamber 11 and the second chamber 12 is formed as space partitioned by the first and second solid electrolyte plates 53 and 55 and the spacer 54. The second reference gas chamber 14 is made up of space partitioned by the second solid electrolyte plate 55 and the spacer 56.

The third electrochemical cell 4 functions as an oxygen density electromotive force type of battery.

In the third electrochemical cell 4, one electrode 41, located as the oxygen sensing electrode for a gas to be measured, is disposed between the first solid electrolyte plate 53 and the porous plate 51. The other electrode 42, which functions as the reference oxygen sensing electrode, is disposed so as to be exposed to the first reference gas chamber 13. The third electrochemical cell 4 is coupled with the oxygen sensing circuit 45 in which the voltmeter 451 is inserted.

The voltmeter 451 measures electromotive force caused between the first and second electrodes 41 and 42. This electromotive force is generated by differences in oxygen concentration between the atmosphere of a gas to be measured and the atmosphere in the first reference gas chamber. This electromotive force provides an output of the third electrochemical cell 4.

The first electrochemical cell 2 has a function as a pumping cell. This cell 2 receives a voltage signal supplied by an electric power source feedback-controlled by pumping current, and pumps oxygen according to a magnitude of the applied voltage between the first chamber 11 and the second reference gas chamber 14.

The first electrochemical cell 2, disposed with the second solid electrolyte plate 55, comprises the measured-gas-side pumping electrode 21 exposed to the first chamber 11 and the reference pumping electrode 22 exposed to the second reference gas chamber 14. Between the electrodes 21 and 22, the pumping circuit 25 in which the ammeter 251 and electric power source 252 are inserted in series is provided. A feedback circuit 255 is provided between the ammeter 251 and the electric power source 252.

Pumping electric current corresponds to the concentration of oxygen present in the first chamber 11. The electric power source 252 is controlled based on an amount of the pumping current using the feedback circuit 255. This control permits the first electrochemical cell 2 to keep the concentration of oxygen in the first chamber 11, that is, in the second chamber 12 communicating with the first one 11, at a constant amount.

The measured-gas-side pumping electrode 21 is an inert electrode against NOx, so that no diffusion gives to NOx.

The second electrochemical cell 3 receives constant voltage of which amount unchanged over time, and measures the concentration of NOx using oxygen-ion current generating due to the constant voltage.

This cell 3, disposed with the first solid electrolyte plate 53, comprises the measured-gas-side sensing electrode 31 exposed to the second chamber 12 and the reference sensing electrode 32 exposed to the first reference gas chamber 13. Between the electrodes 31 and 32, the sensing circuit 35 in which the ammeter 351 and electric power source 352 are inserted in series is provided.

The measured-gas-side sensing electrode 31 is an active electrode which is able to decompose NOx into nitrogen and oxygen. Applying voltage to the second electrochemical cell 3 causes oxygen ions to be yielded on the surface of the measured-gas-side sensing electrode 31, and the oxygen ions communicates as ion current through the first solid electrolyte plate 53. Hence, the ammeter 351 can measure the ion current.

The ion current is proportional to the concentration of NOx contained in the gas to be measured, unless the measured-gas-side pumping electrode 21 of the first electrochemical cell 2 decomposes NOx. As a result, readings of the ammeter 351 provide NOx concentration.

By the way, oxygen contained in the gas to be measured is decomposed on the measured-gas-side sensing electrode 31. However, ion current inherent to NOx can be measured correctly if calibration is made in advance, because the concentration of oxygen in the gas to be measured is substantially kept constant by the first electrochemical cell 2. The calibration is done by measuring a reading of the ammeter 351 in the condition that the concentration of NOx is kept zero.

A capability to measure the $\lambda$-characteristic of the sensing device 1 will now be evaluated.

Both of the sensing device 1 according to the present embodiment and the sensing device 9 according to the conventional technique described using FIG. 1 were incorporated into gas sensors whose configuration is the same, and the gas sensors were disposed in exhaust systems of automobile engines.

With an exhaust gas generated by putting the engines into operation, a $\lambda$-characteristic was measured for each gas sensor in the range of exhaust gas temperatures of 400 to 600° C.

Figure 11:
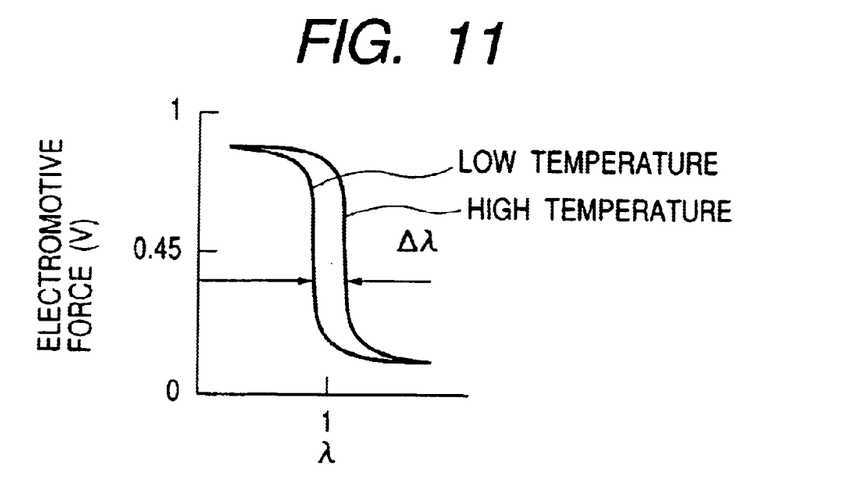
FIG. 11 is a graph explaining temperature dependency of the λ-characteristic.

Because the $\lambda$-characteristic has temperature dependency, the $\lambda$-characteristic behaves differently for each of low and high temperature states, as shown in FIG. 11, if the exhaust gas temperature is raised up to the above amounts. As shown therein, a width $\Delta\lambda$ of the $\lambda$-characteristic was measured during the above temperature range to evaluate this value $\Delta\lambda$ as a capability of the device.

Figure 10:
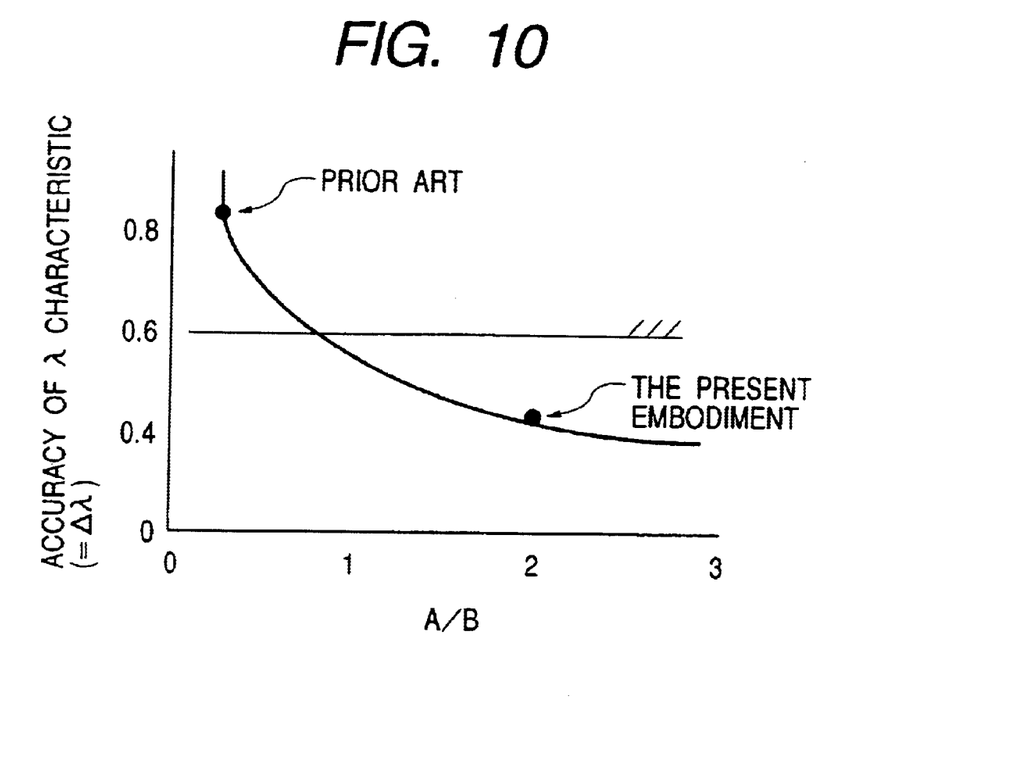
FIG. 10 is a graph showing a comparison between accuracy of the λ-characteristics of the devices according to the fourth embodiment and the conventional configuration.

As a result of the evaluation, as shown in FIG. 10, the conventional gas sensor exhibited that the width $\Delta\lambda=\pm0.08$, while the gas sensor in which the compound layered type of sensing device 1 is incorporated showed that the width $\Delta\lambda=\pm0.04$.

When the width $\Delta\lambda$ exceeds $\pm0.06$, the sensing device, which is employed as the $\lambda$-characteristic measuring gauge used for the exhaust system of automobile engines, decreases its accuracy of detection. As a result, emissions exhausted from automobiles are deteriorated (that is, amounts of emission, such as NOx and HC, increase). It was therefore found that this sensing device 1 was endurable for the above use.

With regard to each of the sensing device 1 according to the present invention and the conventional sensing device 9, two distances A and B were measured. The distance A is taken between both electrodes of the third electrochemical cell. The distance B is taken between the measured-gas-side oxygen sensing electrode of the third electrochemical cell and a nearest other electrode (i.e., the reference pumping electrode or the measured-gas-side pumping electrode). Both distances A and B are not straight ones, but each distance is a path along which ion current flows between the solid electrodes.

As can be understood from FIG. 10, the conventional sensing device 9 shows that A/B=0.25, while the sensing device 1 according to the present invention shows that A/B=2.

Further, various types of compound layered type of sensing devices were manufactured, and relationships between the accuracy of the $\lambda$-characteristic for each sensing device and the ratio A/B thereof were measured. The solid curved line of FIG. 10 expresses a correlation between accuracy and ratio.

It is therefore understood that, when the device configuration according to the present invention is employed, the $\lambda$-characteristic is measurable with precision and its measurement accuracy can be improved by increasing the ratio A/B.

The advantages of the fourth embodiment are given as follows. First, both sensing electrodes 41 and 42 of the third electrochemical cell 4 are close to each other, the inner resistance of the third electrochemical cell 4 becomes smaller, so that the concentration of oxygen can be measured at higher accuracy.

Additionally, such a lower amount of the inner resistance can reduce influence of outside atmospheric temperature. The concentration of oxygen can be measured with less temperature dependency.

Further, it is the second electrochemical cell 3 that is disposed with the first solid electrolyte plate 53 with which the third electrochemical cell 4 is disposed as well. Because the voltage applied to the second electrochemical cell 3 is constant over time, the measurement accuracy of the third electrochemical cell 4 has not so much influence from the second electrochemical cell 3.

Still further, the first electrochemical cell 2 is located with the second solid electrolyte plate 55 located with both first chamber 11 and first solid electrolyte plate 53 layered thereon. The third electrochemical cell 4 has little influence of the fluctuating voltage applied to the first electrochemical cell 2.

This enables higher accuracy of measurement of the third electrochemical cell 4, whereby increasing the measurement accuracy of the $\lambda$-characteristic.

Therefore, it is possible to provide a compound layered type of sensing device superior in the measurement accuracy of the $\lambda$-characteristic.

Figure 12:
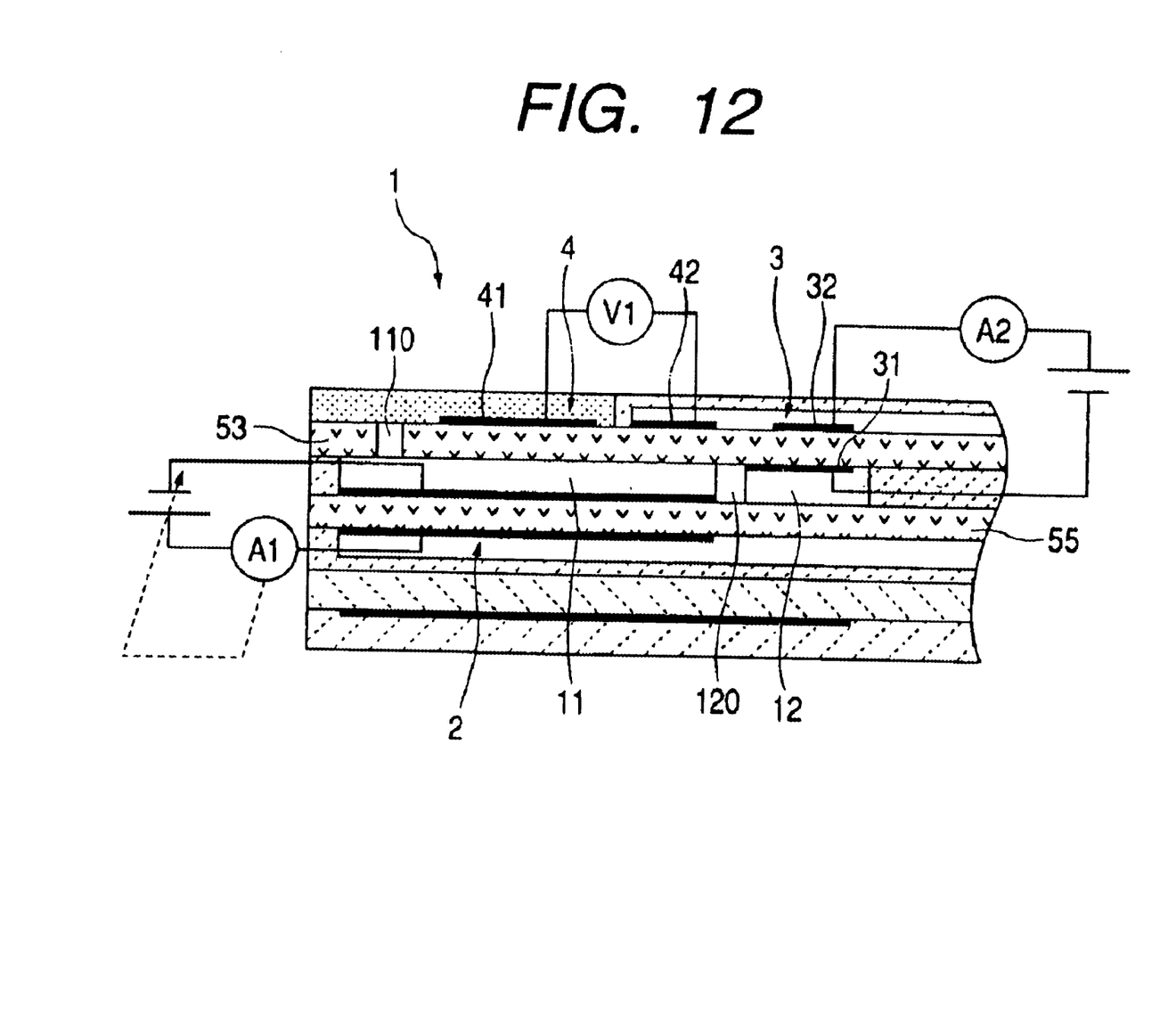
FIG. 12 shows a modification of a compound layered type of sensing element according to the fourth embodiment.
Figure 13:
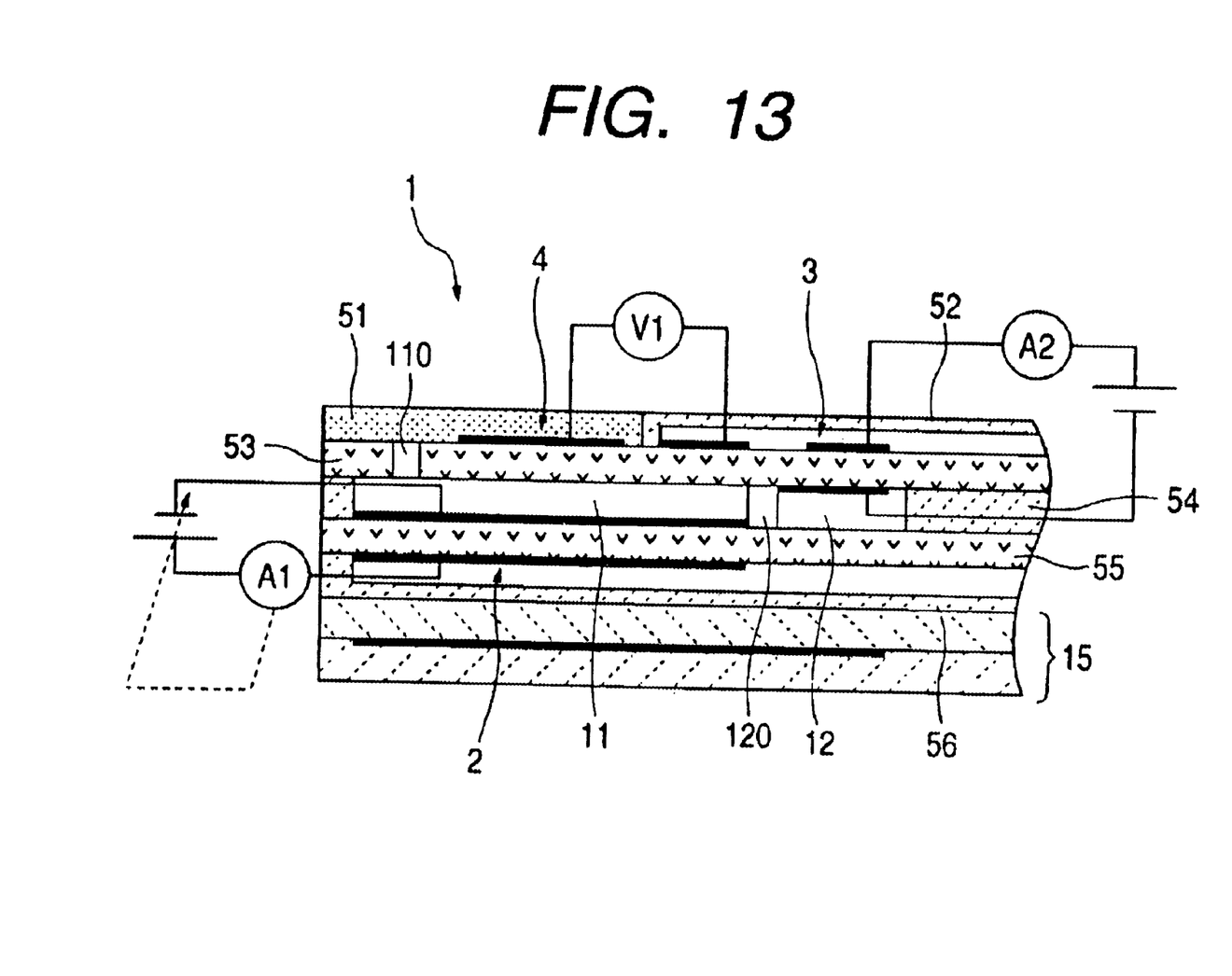
FIG. 13 shows another modification of a compound layered type of sensing element according to the fourth embodiment.

Modifications of the compound layered type of sensing device 1 according to the present embodiment are provided in FIGS. 12 and 13.

In a compound layered type of sensing device 1 shown in FIG. 12, both of the reference oxygen sensing electrode 41 of the third electrochemical cell 4 and the reference sensing electrode 32 of the second electrochemical cell 3 are formed from a single electrode. The remaining constituents are formed in a similar manner to those shown in FIG. 2.

In a compound layered type of sensing device 1 shown in FIG. 13, the porous plate 51, spacers 52, 54 and 56, first and second solid electrolyte plates 53 and 55, and heater 15 are all made of an oxygen-ion conductive zirconia ceramic material. The remaining constituents are formed in a similar manner to those shown in FIG. 8.

In consequence, the devices 1 shown in the above modifications are able to provide the similar advantages to those gained in the fourth embodiment.

The foregoing embodiments explain the sensing device capable of measuring the concentration of NOx, but an object to be measured is not confined to NOx. Alternatively, appropriately changing types of the measured-gas-side sensing electrode at the second electrochemical cell 3 makes it possible to measure the concentration of HC or CO.

Although the description above contains many specificities, these should not be construed as limiting the scope of the invention but as merely providing illustrations of some of the presently preferred embodiments of the present invention. Thus the scope of the present invention should be determined by the appended claims and their equivalents.

What we claim is:

1. A compound layered type of sensing device, comprising:
   a plurality of solid electrolyte plates;
   a plurality of pairs of electrodes, wherein each pair of electrodes is disposed on at least one surface of one of the plurality of solid electrolyte plates, forming first to third electrochemical cells, wherein a gas to be measured is pre-processed under oxygen pumping carried out by the first electrochemical cell, a concentration of a particular gas component of the gas to be measured being detected by the second electrochemical cell and a difference in electromotive force between the gas to be measured and a reference gas being detected by the third electrochemical cell;
   first and second chambers formed in the device, the gas to be measured being introduced into the first and second chambers; and
   a fourth electrochemical cell configured to detect a concentration of oxygen of the gas to be measured present in at least one of the first and second chambers,
   wherein a single pair of electrodes of the third electrochemical cell is disposed on the same surface of one of the plurality of solid electrolyte plates, and the first and third electrochemical cells are located on mutually different solid electrolyte plates of the plurality of solid electrolyte plates.

2. The sensing device of claim 1, wherein the first chamber is formed to communicate with an outside of the device via a first diffusive resistance passage and the second chamber is formed to communicate with the first chamber via a second diffusive resistance passage, wherein
   one of the two electrodes of the first electrochemical cell is located to be exposed to the first chamber so that the first electrochemical cell permits a given amount of oxygen to be introduced into or from the first chamber corresponding to an amount of voltage applied to the first electrochemical cell, and
   one of the two electrodes of the second electrochemical cell is located to be exposed to the second chamber so that applying a given amount of voltage to the electrodes of the second electrochemical cell permits the second electromechanical cell to detect current corresponding to the concentration of a particular gas component of the gas to be measured.

3. The sensing device of claim 2, wherein one of the two electrodes of the first electrochemical cell and one of the two electrodes of the third electrochemical cell are located to be exposed to mutually different reference gas chambers of the plurality of reference gas chambers.

4. The sensing device of claim 2, further comprising a plurality of reference gas chambers formed in the device,
   wherein one of the two electrodes of the first electrochemical cell and one of the two electrodes of the third electrochemical cell are located to be exposed to mutually different reference gas chambers of the plurality of reference gas chambers.

5. The sensing device of claim 2, wherein one of the two electrodes of the fourth electrochemical cell is located to be exposed to either one of the first and second chambers.

6. The sensing device of claim 2, wherein one of the two electrodes of the fourth electrochemical cell is located to be exposed to the second chamber.

7. The sensing device of claim 1, further comprising first and second reference gas chambers formed in the device,
   wherein one of the two electrodes of the second electrochemical cell and one of the two electrodes of the fourth electrochemical cell are located to be exposed to the same reference gas chamber of the first and second reference gas chambers and the other of the two electrodes of the second electrochemical cell and the other of the two electrodes of the fourth electrochemical cell are located to be exposed to either one of the first and second chambers.

8. The sensing device of claim 7, wherein one of the two electrodes of the first electrochemical cell and one of the two electrodes of the third electrochemical cell are located to be exposed to mutually different reference gas chambers of the plurality of reference gas chambers.

9. The sensing device of claim 1, further comprising a plurality of reference gas chambers formed in the device,
   wherein one of the two electrodes of the first electrochemical cell and one of the two electrodes of the third electrochemical cell are located to be exposed to mutually different reference gas chambers of the plurality of reference gas chambers.

10. The sensing device of claim 1, wherein one of the two electrodes of the second electrochemical cell is located to be exposed to the second chamber and one of the two electrodes of the fourth electrochemical cell is located to be exposed to either one of the first and second chambers.

11. The sensing device of claim 1, wherein one of the two electrodes of the second electrochemical cell and one of the two electrodes of the fourth electrochemical cell are located to be exposed to the second chamber.

12. A compound layered type sensing device, comprising:
    first and second solid electrolyte plates;
    first and second chambers, each formed between the first and second solid electrolyte plates, into which a gas to be measured is introduced respectively, the first chamber air outside the device via a first diffusive resistance passage and the second chamber being connected to the first chamber via a second diffusive resistance passage;
    first and second reference gas chambers into which a reference gas is introduced respectively, the first reference gas chamber being formed on one side of the first solid electrolyte plate opposite to the first and second chambers, and the second reference gas chamber being formed on one side of the second solid electrolyte plate opposite to the first and second chambers;
    a first pair of electrodes comprising a pumping electrode and a reference pumping electrode to form a first electrochemical cell together with the second solid electrolyte plate, wherein the pumping electrode is located on the second solid electrolyte plate to be exposed to the first chamber and the reference pumping electrode is located to be exposed to the second reference gas chamber, whereby the first electrochemical cell pumps oxygen corresponding to an amount of voltage applied to the electrodes of the first electrochemical cell;
    a second pair of electrodes comprising a sensing electrode and a reference sensing electrode to form a second electrochemical cell together with the first solid electrolyte plate, wherein the sensing electrode is located on the first solid electrolyte plate to be exposed to the second chamber and the reference sensing electrode is located to be exposed to the first reference gas chamber, whereby the second electrochemical cell produces current corresponding to a concentration of a particular gas component of the gas to be measured by applying a given amount of voltage to the electrodes of the second electrochemical cell; and a third pair of electrodes comprising an oxygen sensing electrode and a reference oxygen sensing electrode to form a third electrochemical cell together with the first solid electrolyte plate, wherein the oxygen sensing electrode is located on a given surface of the first solid electrolyte plate to communicate with air outside the device and the reference oxygen sensing electrode is located on the given surface of the first solid electrolyte plate to be exposed to the first reference gas chamber, whereby the third electrochemical cell measures oxygen of the gas to be measured between the electrodes thereof.

13. A compound layered type of sensing device, comprising:

a plurality of solid electrolyte plates;

a plurality of pairs of electrodes, wherein each pair of electrodes is disposed on at least one surface of one of the plurality of solid electrolyte plates, forming first to third electrochemical cells, wherein a gas to be measured is pre-processed under oxygen pumping carried out by the first electrochemical cell, a concentration of a particular gas component of the gas to be measured being detected by the second electrochemical cell and a difference in electromotive force between the gas to be measured and a reference gas being detected by the third electrochemical cell; and a heater disposed to provide the solid electrolyte plates with heat, wherein a single pair of electrodes of the third electrochemical cell is disposed on the same surface of one of the plurality of solid electrolyte plates, and the first and third electrochemical cells are located on mutually different solid electrolyte plates of the plurality of solid electrolyte plates and the second electrochemical cell is positionally more distant from the heater than the first electrochemical cell.

* * * * *